(12) United States Patent
Merillon et al.

(10) Patent No.: US 9,757,340 B2
(45) Date of Patent: Sep. 12, 2017

(54) SOLID UNIT WITH HIGH FEXOFENADINE CONTENT AND PROCESS FOR THE PREPARATION THEREOF

(71) Applicant: SANOFI, Paris (FR)

(72) Inventors: Baptiste Merillon, Paris (FR);
Jean-Yves Lanne, Paris (FR); Marie Renouard, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/651,621

(22) PCT Filed: Dec. 20, 2013

(86) PCT No.: PCT/EP2013/077752
§ 371 (c)(1),
(2) Date: Jun. 11, 2015

(87) PCT Pub. No.: WO2014/096387
PCT Pub. Date: Jun. 26, 2014

(65) Prior Publication Data
US 2015/0313885 A1 Nov. 5, 2015

(30) Foreign Application Priority Data

Dec. 21, 2012 (FR) ..................................... 12 62647

(51) Int. Cl.
*A61K 31/445* (2006.01)
*A61K 9/20* (2006.01)
(52) U.S. Cl.
CPC .......... *A61K 9/2031* (2013.01); *A61K 9/2077* (2013.01); *A61K 9/2095* (2013.01); *A61K 31/445* (2013.01)

(58) Field of Classification Search
CPC .................................................... A61K 31/455
See application file for complete search history.

(56) References Cited

U.S. PATENT DOCUMENTS

| | | | |
|---|---|---|---|
| 6,113,942 A | 9/2000 | Ortyl et al. | |
| 2003/0099700 A1* | 5/2003 | Faham | A61K 9/0056 424/465 |
| 2015/0374622 A1 | 12/2015 | Daste et al. | |

FOREIGN PATENT DOCUMENTS

| | | |
|---|---|---|
| EP | 0 173 293 A2 | 3/1986 |
| EP | 1 454 635 A1 | 9/2004 |
| WO | WO-2011/151733 A2 | 12/2011 |
| WO | WO-2011/151733 A3 | 12/2011 |

OTHER PUBLICATIONS

International Search Report mailed on Feb. 10, 2014, for PCT Patent Application No. PCT/EP2013/077752, filed on Dec. 20, 2013, three pages.

* cited by examiner

*Primary Examiner* — Samira Jean-Louis
(74) *Attorney, Agent, or Firm* — Morrison & Foerster LLP

(57) ABSTRACT

The present invention relates to pharmaceutical compositions intended to be used in the form of a solid unit such as a tablet, for oral administration, comprising a high content of fexofenadine and/or of at least one pharmaceutically acceptable salt thereof, and also to hot-melt processes for manufacturing solid units.

19 Claims, No Drawings

SOLID UNIT WITH HIGH FEXOFENADINE CONTENT AND PROCESS FOR THE PREPARATION THEREOF

CROSS-REFERENCE TO RELATED APPLICATIONS

This application is a National Phase application under 35 U.S.C. §371 of International Application No. PCT/EP2013/077752 filed Dec. 20, 2013, which claims priority to French Application No. 1262647 filed Dec. 21, 2012, the disclosures of each of which are incorporated herein by reference in their entirety.

The present invention relates to pharmaceutical compositions intended to be used for oral administration comprising predominantly fexofenadine and/or at least one pharmaceutically acceptable salt thereof, such as fexofenadine hydrochloride, and also to solid units as such manufactured from said compositions, preferably tablets. The present invention also relates to a hot-melt process for preparing such solid units and also relates to the therapeutic use of such solid units.

Fexofenadine is a well-known antihistamine compound which has a selective peripheral H1 receptor antagonist activity. Fexofenadine is normally used as an active ingredient in the form of fexofenadine hydrochloride, of formula (I) below:

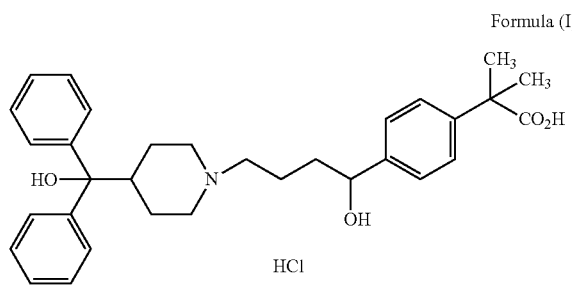

Formula (I)

Fexofenadine hydrochloride can be administered by means of dosage units containing an effective amount of said active ingredient, for example 60 mg, 120 mg or 180 mg of fexofenadine hydrochloride for an adult, or else 30 mg of fexofenadine hydrochloride for a child.

For example, fexofenadine hydrochloride is commercially available as the brand Allegra®.

For use thereof as a medicament, fexofenadine or a pharmaceutically acceptable salt thereof, such as, for example, the hydrochloride, is advantageously formulated in the form of orally administered solid units.

The term "solid unit" is intended to mean in the present application a solid and unitary, i.e. unfractionated, galenic form, corresponding to a dose of medicaments. Such solid units are orally administerable and are, for example, tablets, pills, dragees (also known as "sugar-coated tablets"), chewing gums, lozenges, capsules or gel capsules. In particular, powder and granules are not solid units for the purposes of the present application. Preferably, such solid units are tablets. The tablets according to the invention may optionally be coated. The term "coating" is intended to mean any treatment aimed at depositing at least one layer on the tablet. By way of particular examples of coating, mention may be made of film-coating or sugar-coating.

Currently, the manufacturing of a fexofenadine hydrochloride tablet involves a step of wet granulation of the fexofenadine hydrochloride. U.S. Pat. No. 6,113,942 describes such a process. The addition of the excipients required for the compression of these grains results in a final weight of 600 mg per unit.

The characteristics of fexofenadine hydrochloride are among the factors which limit the possibilities of increasing its concentration within the solid units. The fexofenadine hydrochloride tablet on the market comprises a maximum of 30% by weight of fexofenadine hydrochloride relative to the total weight of said tablet.

Furthermore, wet granulation produces unsatisfactory dust emission levels during the manufacture of solid galenic forms, the emission of dust being subsequent to a drying phase that is essential in such a process.

The applicant has established, surprisingly, that it is possible to prepare a pharmaceutical composition with a high content of fexofenadine and/or of at least one pharmaceutically acceptable salt thereof, such as fexofenadine hydrochloride, which makes it possible to form orally administerable solid units. This capacity to increase the content of fexofenadine and/or of at least one pharmaceutically acceptable salt thereof, such as fexofenadine hydrochloride, within a solid unit, makes it possible to reduce the size of said solid unit, advantageously a tablet, relative to the galenic form currently on the market. A hot-melt process for manufacturing a solid unit or solid units which has the advantage of allowing an increase in the concentration of active ingredient has also been developed.

This process via hot-melt granulation has, furthermore, the advantage of overcoming the problems normally encountered in the context of a process via wet granulation. Indeed, this process makes it possible to have a significantly reduced water content in the galenic form compared with the use of a conventional process, the drying step thus being avoided. The elimination of this drying step makes it possible not only to simplify the process, but especially to make it less energy-consuming. This results in time saving and a reduction in costs.

In addition, it makes it possible to obtain grains based on a composition rich in fexofenadine and/or in at least one pharmaceutically acceptable salt thereof, such as fexofenadine hydrochloride. These grains are, furthermore, directly compressible after they have been obtained, which allows the implementation of a continuous process for industrial manufacture of solid units, in particular tablets, allowing savings to be made in terms of time and cost at the industrial production level.

The reduction in the size of the solid unit as galenic form has several advantages:
  it makes it possible to significantly improve the patient's comfort and the adherence to the treatment; this is because the solid unit, such as, for example, a tablet, is more easily ingested by the patient,
  it makes it possible to reduce industrial production costs, in particular by virtue of the decrease in the amount of excipients used and of the decrease in the boxes and packaging and therefore in the number of transportation pallets.

A subject of the invention is a solid unit comprising a dose of 5 to 500 mg of fexofenadine and/or of at least one pharmaceutically acceptable salt thereof, the composition of which is the following:
  45% to 92% by weight of fexofenadine and/or of at least one pharmaceutically acceptable salt thereof, optionally in combination with at least one other active ingredient, 4% to 20% by weight of a hot-melt excipient or mixture of hot-melt excipients, said hot-melt excipient(s) having a melting point or a glass transition temperature greater than or equal to approximately 35° C. and less than or equal to approximately 115° C., and 4% to 50% by weight of an additional excipient or of a plurality (or mixture) of additional excipients, the percentages by weight being expressed relative to the total weight of the composition, the sum of the percentages by weight of each ingredient having to reach 100%.

It will be noted that, in the context of the present application, and unless otherwise stipulated, the ranges of values indicated are understood to be limits included.

Preferably, the solid unit comprises a dose of 25 to 300 mg of fexofenadine and/or of at least one pharmaceutically acceptable salt thereof, more preferentially, in particular, a dose of 30, 60, 120 or 180 mg.

Advantageously, the fexofenadine is present in the composition in the form of a salt, namely fexofenadine hydrochloride as presented in formula (I) above. This salt exists in three different forms depending on the degree of hydration of said salt. Preferably, the fexofenadine hydrochloride is in form I, i.e. in the anhydrous form.

Preferably, the percentage by weight of fexofenadine and/or of at least one pharmaceutically acceptable salt thereof, such as fexofenadine hydrochloride, is between 65% and 92%, more preferentially between 68% and 92% by weight and even more preferentially between 70% and 92% by weight. According to one alternative preferential embodiment, the percentage by weight of fexofenadine and/or of at least one pharmaceutically acceptable salt thereof, such as fexofenadine hydrochloride, is between 50% and 92%, more preferentially between 55% and 92% and even more preferentially between 60% and 92%.

The term "excipient" covers, in the present application, an inactive or inert substance which facilitates the preparation and the administration of a medicament.

In the present application, two main types of excipients are distinguished: the hot-melt excipients, used to form grains of active ingredients via the hot-melt route, and the additional excipient(s) used to improve the properties of the solid unit or to facilitate the implementation of the process for manufacturing same.

The expression "4% to 50% by weight of the plurality (or mixture) of additional excipients" is intended to mean that the content of 4% to 50% is the content for the whole of the additional excipients.

The expression "active ingredient which can be combined with fexofenadine and/or at least one pharmaceutically acceptable salt thereof" covers more particularly:

decongestants such as ephedrine, pseudoephedrine and/or phenylephrine, and/or anti-inflammatories, preferably nonsteroidal anti-inflammatory drugs (NSAIDs) of the propionic acid derivative class, such as naproxen, ibuprofen and/or ketoprofen.

Advantageously, the fexofenadine hydrochloride can be combined with phenylephrine, with pseudoephedrine or with pseudoephedrine and naproxen.

Preferably, the percentage by weight of the hot-melt excipient(s) having a melting point or a glass transition temperature greater than or equal to 35° C. and less than or equal to 115° C. is included in the range of from 4% to 17% by weight, more preferentially from 4% to 15% by weight and even more preferentially from 4% to 10%. This percentage hot-melt excipient range is particularly advantageous since it allows the compression of fexofenadine and/or of at least one pharmaceutically acceptable salt thereof using a small amount of additional excipient(s) while at the same time maintaining an acceptable dissolution of the solid unit. It is therefore important for the total content of the excipient(s) used as hot-melt excipient to be no greater than 20%, preferably no greater than 17% and more preferentially no greater than 15%.

Moreover, the percentage by weight of the additional excipient(s) is preferentially included in the range of from 4% to 15%. According to one alternative preferential embodiment, the percentage by weight of the additional excipient(s) is preferentially included in the range of from 4% to 35% and more preferentially in the range of from 4% to 30%.

According to a first preferential embodiment, the solid unit has the following specific composition:

65% to 92% by weight of fexofenadine and/or of at least one pharmaceutically acceptable salt thereof, optionally in combination with at least one other active ingredient, 4% to 20% by weight of a hot-melt excipient or mixture of hot-melt excipients, said hot-melt excipient(s) having a melting point or a glass transition temperature greater than or equal to approximately 35° C. and less than or equal to approximately 115° C., and 4% to 15% by weight of an additional excipient or of a plurality of additional excipients, the percentages by weight being expressed relative to the total weight of the composition, the sum of the percentages by weight of each ingredient having to reach 100%.

According to a second preferential embodiment, the solid unit has the following specific composition:

68% to 92% by weight of fexofenadine and/or of at least one pharmaceutically acceptable salt thereof, optionally in combination with at least one other active ingredient, 4% to 17% by weight of a hot-melt excipient or mixture of hot-melt excipients, said hot-melt excipient(s) having a melting point or a glass transition temperature greater than or equal to approximately 35° C. and less than or equal to approximately 115° C., and 4% to 15% by weight of an additional excipient or of a plurality of additional excipients, the percentages by weight being expressed relative to the total weight of the composition, the sum of the percentages by weight of each ingredient having to reach 100%.

According to a third preferential embodiment, the solid unit has the following specific composition:

70% to 92% by weight of fexofenadine and/or of at least one pharmaceutically acceptable salt thereof, optionally in combination with at least one other active ingredient, 4% to 15% by weight of a hot-melt excipient or mixture of hot-melt excipients, said hot-melt excipient(s) having a melting point or a glass transition temperature greater than or equal to approximately 35° C. and less than or equal to approximately 115° C., and 4% to 15% by weight of an additional excipient or of a plurality of additional excipients, the percentages by weight being expressed relative to the total weight of the composition, the sum of the percentages by weight of each ingredient having to reach 100%.

According to a fourth preferential embodiment, the solid unit has the following specific composition:

50% to 92% by weight of fexofenadine and/or of at least one pharmaceutically acceptable salt thereof, optionally in combination with at least one other active ingredient, 4% to 15% by weight of a hot-melt excipient or mixture of hot-melt excipients, said hot-melt excipient(s) having a melting point or a glass transition temperature greater than or equal to approximately 35° C. and less than or equal to approximately 115° C., and 4% to 35% by weight of an additional excipient or of a plurality of additional excipients, the percentages by weight being expressed relative to the total weight of the composition, the sum of the percentages by weight of each ingredient having to reach 100%.

According to a fifth preferential embodiment, the solid unit has the following specific composition:

60% to 92% by weight of fexofenadine and/or of at least one pharmaceutically acceptable salt thereof, optionally in combination with at least one other active ingredient, 4% to 10% by weight of a hot-melt excipient or mixture of hot-melt excipients, said hot-melt excipient(s) having a melting point or a glass transition temperature greater than or equal to approximately 35° C. and less than or equal to approximately 115° C., and 4% to 30% by weight of an additional excipient or of a plurality of additional excipients, the percentages by weight being expressed relative to the total weight of the composition, the sum of the percentages by weight of each ingredient having to reach 100%.

The fexofenadine and/or at least one pharmaceutically acceptable salt thereof, and also the hot-melt excipient(s), are the main ingredients which will make it possible to form grains. These grains constitute the "internal" phase of the solid unit. They can also comprise at least one additional excipient such as a disintegrant and/or the other active ingredient(s) combined with the fexofenadine and/or at least one pharmaceutically acceptable salt thereof.

The term "hot-melt excipient" is intended to mean an excipient which softens or becomes fluid under the effect of heat. Such excipients, for the purposes of the present application, have either a melting point (temperature at which the crystalline solid state and the liquid state of the excipient coexist, measured at normal atmospheric pressure of 1 atmosphere) or a glass transition temperature (temperature below which the molecules forming the excipient have a low relative mobility or temperature at which the excipient goes from the amorphous solid state to a viscous fluid state) included in the range of from 35° C. to 115° C. Preferably, said point or temperature is included in the range of from 35° C. to 100° C. and even more preferentially in the range of from 50° C. to 100° C.

The measurement of the melting point or of the glass transition temperature is a measurement well known to those skilled in the art. It is usually carried out by differential scanning calorimetry (DSC), using a differential scanning calorimeter.

The melting points (abbreviated as Mp) or the glass transition temperatures (abbreviated as Tg) are given below by way of indication and are not limiting. They come mostly from the "Handbook of Pharmaceutical Excipients", fifth edition, Pharmaceutical Press.

As hot-melt excipient that is particularly suitable for the invention, mention may be made of citric acid monohydrate (Mp±100° C.), stearic acid (Mp±54-67° C.), palmitic acid (Mp±63-64° C.), lauric acid (Mp±43° C.), myristic acid (Mp±48-55° C.), hydrogenated castor oil (Mp±83-88° C.), hydrogenated vegetable oil (Mp±57-70° C.), stearyl alcohol (Mp±57-70° C.), cetostearyl alcohol (Mp±49-56° C.), cetyl alcohol (Mp±47-53° C.), vanillin (Mp±76-78° C.), amorphous chlorocresol (Mp±64-67° C.), cetyl pyridinium hydrochloride (Mp±80-84° C.), sorbitan monostearate (Mp±43-48° C.), sorbitan monopalmitate (Mp±53-57° C.), xylitol (Mp±92-96° C.), dextrose (Mp±83° C.), ethylmaltol (Mp±89-93° C.), butylated hydroxyanisole (Mp±47° C.), benzalkonium hydrochloride (Mp±40° C.), ascorbyl palmitate (Mp±107-117° C.), sorbitol (Mp±93-112° C.), anhydrous raffinose (Mp±80-118° C.), phenylmercuric borate (Mp±112-113° C.), polyethylene glycols (abbreviated as PEG) such as PEG 3000 (Mp±48-54° C.), PEG 4000 (Mp±50-58° C.), PEG 6000 (Mp±55-63° C.), PEG 8000 (Mp±60-63° C.) and PEG 20 000 (Mp±60-63° C.), polyethylene oxides (Mp±65-70° C.), polyethylene/propylene glycol copolymers, such as poloxamer 188 (Mp±52° C.), poloxamer 237 (Mp±50° C.), poloxamer 338 (Mp±57° C.) or poloxamer 407 (Mp±56° C.), glyceryl monostearate (Mp±55° C.), glyceryl palmitostearate (Mp±52-55° C.), glyceryl behenate (Mp±65-77° C.), for instance Compritol®888 ATO, waxes, for instance carnauba wax (Mp±80-88° C.), microcrystalline wax (Mp±54-102° C.), white wax or yellow wax (Mp±61-65° C.), beeswax (Mp±61-65° C.), sodium acetate trihydrate (Mp±58° C.), polymethacrylates, in particular Eudragit® E (Tg±48° C.), polyvinyl acetate phthalate (Tg±42.5° C.), carbomers (Tg±100-105° C.), polycarbophils (Tg±100-105° C.), hypromellose acetate succinate (Tg±105° C.), copovidone (Tg±106° C.), and mixtures thereof.

For the purposes of the present application, the term "hydrogenated vegetable oil" covers soybean oil, cottonseed oil and/or palm oil.

Advantageously, the hot-melt excipient(s) is (are) chosen from stearic acid, palmitic acid, hydrogenated castor oil, hydrogenated vegetable oil, stearyl alcohol, vanillin, amorphous chlorocresol, cetyl pyridinium hydrochloride, sorbitan monopalmitate, xylitol, dextrose, ethylmaltol, ascorbyl palmitate, sorbitol, anhydrous raffinose, phenylmercuric borate, polyethylene glycols (abbreviated as PEG), polyethylene oxides, polyethylene/propylene glycol copolymers, such as poloxamer 188, poloxamer 237, poloxamer 338, or poloxamer 407, glyceryl monostearate, glyceryl palmitostearate, glyceryl behenate, waxes, for instance carnauba wax, microcrystalline wax, white wax or yellow wax, beeswax, sodium acetate trihydrate, polymethacrylates, in particular Eudragit® E, carbomers, polycarbophils, hypromellose acetate succinate, and mixtures thereof.

Preferably, the hot-melt excipient(s) is (are) chosen from stearic acid, palmitic acid, hydrogenated castor oil, xylitol, polyethylene glycols (abbreviated as PEG), polyethylene oxides, polyethylene/propylene glycol copolymers, such as poloxamer 188, poloxamer 237, poloxamer 338 or poloxamer 407, glyceryl monostearate, glyceryl palmitostearate, glyceryl behenate, carnauba wax, microcrystalline wax, white wax or yellow wax, beeswax, polymethacrylates, in particular Eudragit® E, and mixtures thereof.

Even more preferentially, the hot-melt excipient(s) is (are) chosen from polyethylene/propylene glycol copolymers, polyethylene glycols (such as PEG 4000, PEG 6000 and PEG 8000), stearic acid, polyethylene oxides, glyceryl palmitostearate, and mixtures thereof.

Advantageously, the hot-melt excipient(s) has (have) a viscosity at 100° C. with a shear of $0.1\ s^{-1}$ of less than 3000 mPa·s, preferably less than 2000 mPa·s or more preferentially than 1000 mPa·s.

The measurement of the viscosity is a measurement well known to those skilled in the art. In the present case, it is carried out using a rheometer (of Anton Paar type). The hot-melt excipient is brought to the desired working temperature, namely 100° C. for the present measurement, prior to the measurement. It is subsequently introduced into a cylindrical container thermostatted at the desired working temperature, so as to be subjected to, therein, a shear ramp (from $0.1\ s^{-1}$ to $100\ s^{-1}$) applied by means of a coaxial module.

Preferably, the hot-melt excipient(s) is (are) water soluble.

According to one advantageous embodiment, the ratio of the fexofenadine and/or of at least one pharmaceutically acceptable salt thereof, such as fexofenadine hydrochloride, to the hot-melt excipient(s) is between 3.5 and 15, preferably between 5 and 12, more preferentially between 8 and 10 or, according to one alternative preferential embodiment, between 7 and 10.

The additional excipients are predominantly used to form the "external" phase, i.e. the phase into which the grains or internal phase will be incorporated.

Advantageously, the additional excipient(s) is (are) chosen from the group consisting of disintegrants, flow agents, lubricants and/or diluents.

In the present application, a disintegrant is an excipient which allows satisfactory crumbling of the solid unit in the stomach, for example by modifying one or more parameters such as the hardness of the solid unit and/or the penetration of water into the solid unit.

Advantageously, the disintegrant is chosen from the group consisting of crosslinked polyvinylpyrrolidone, crosslinked carboxymethylcellulose, alginic acid, sodium alginate, sodium carboxymethylcellulose, microcrystalline cellulose, powdered cellulose, sodium croscarmellose, crospovidone, pregelatinized starch, sodium carboxymethyl starch, starch, and mixtures thereof. Preferably, the disintegrants are chosen from the group consisting of sodium croscarmellose, crospovidone, pregelatinized starch, microcrystalline cellulose, sodium carboxymethyl starch (preferably of type A or B), and mixtures thereof, more preferentially sodium croscarmellose, crospovidone, and mixtures thereof.

In the group of disintegrants, one particular group of disintegrants can be distinguished: the superdisintegrants. The superdisintegrants are so named because of their high efficiency, even at low concentration, and because of their strong capacity to swell in the presence of water. Advantageously, the superdisintegrants are chosen from the group consisting of sodium croscarmellose, crospovidone and sodium carboxymethyl starch (preferably of type A or B).

The term "flow agent" covers more particularly, in the present application, an excipient intended to facilitate the flow of particles, such as mixtures of powders, in processes for manufacturing galenic forms and in particular solid units.

Advantageously, the flow agent is chosen from the group consisting of silicon dioxide, preferably colloidal silica, magnesium trisilicate, talc, and mixtures thereof.

For the purposes of the present application, a lubricant is an excipient intended to facilitate the manufacture of the solid units, by improving the fluidity of the particles, such as the grains or powders, by reducing inter-particle friction and by decreasing adhesion of the particles to the piping of the machines.

Advantageously, the lubricant is chosen from the group consisting of sodium stearylfumarate, calcium stearate, magnesium stearate, zinc stearate, sodium benzoate, talc, and mixtures thereof. The lubricant is preferably magnesium stearate.

For the purposes of the present application, a diluent is an excipient used for the manufacture of galenic forms and in particular of solid units. It is introduced with the main objective of diluting the active ingredient within the composition until a satisfactory weight is obtained. However, it can also contribute to improving certain properties during manufacturing, for instance the flow of the composition, or the cohesion or the crumbling (or disintegration) of the solid unit.

Since the objective of the invention is to reduce the weight of the solid unit as far as possible, it is understood that the presence of diluent is to be avoided. However, it is possible to introduce diluent to a certain extent, in a content of less than or equal to 40%. The diluent content is preferably equal to 0.

Advantageously, the diluent is chosen from the group consisting of lactose, celluloses, preferably microcrystalline cellulose, starch, pregelatinized starch, polyols with a melting point greater than 115° C., sucrose, trehalose, calcium phosphate, calcium carbonate, and mixtures thereof.

According to one preferential embodiment, at least one additional excipient is a disintegrant, introduced into the composition in a content of between 4% and 15% by weight and preferably 5% to 12% by weight relative to the total weight of the composition. As indicated above, this disintegrant may be a simple disintegrant (i.e. a disintegrant which does not belong to the superdisintegrant group) or a superdisintegrant.

More preferentially, the composition comprises a second disintegrant, which is a superdisintegrant, introduced into the composition in a content of between 0.5% and 15% by weight and more preferentially between 0.5% and 12% by weight relative to the total weight of the composition.

Advantageously, the total content of disintegrant(s) in the composition is between 4% and 30% by weight relative to the total weight of the composition.

It will be noted that, in the present application, when an additional excipient has several functionalities, it can be introduced in a content greater than that associated with a single given functionality. This is the case, for example, with microcrystalline cellulose, which has the functions of disintegration and diluent and which can be introduced in a content greater than 15%, which represents the maximum content of a disintegrant according to a preferential embodiment.

Preferably, the additional excipients are:
- at least one disintegrant chosen from crospovidone, sodium croscarmellose and/or sodium carboxymethyl starch, microcrystalline cellulose,
- a lubricant: magnesium stearate,
- a flow agent: colloidal silica, and/or
- a diluent chosen from lactose and/or microcrystalline cellulose.

Preferably, the additional excipients are:
- at least one disintegrant chosen from crospovidone, sodium croscarmellose and/or microcrystalline cellulose,
- a lubricant: magnesium stearate,
- a flow agent: colloidal silica, and/or
- a diluent chosen from lactose and/or microcrystalline cellulose.

More preferentially, the additional excipients are:

at least one disintegrant chosen from crospovidone, sodium croscarmellose and/or microcrystalline cellulose, a lubricant: magnesium stearate, and/or a flow agent: colloidal silica.

The solid unit according to the invention may also comprise a coating, such as a film-coating, for example with various polymers and/or other appropriate materials. By way of examples of polymers or other appropriate materials, mention may be made of hydroxypropylmethylcellulose, polyethylene glycol, polyvinyl acetate, polyvinyl alcohol, triacetin, titanium dioxide, talc, etc.

According to one preferential embodiment, the solid unit is an optionally film-coated tablet. In particular, the tablet may be a single-layer or multilayer tablet. A multilayer tablet may be advantageous when at least one active ingredient is combined with fexofenadine and/or with at least one pharmaceutically acceptable salt thereof. In such a case, the fexofenadine and/or at least one pharmaceutically acceptable salt thereof is introduced into a first layer, and the combined active ingredient is introduced into a second layer, it being possible for a dividing layer to be additionally added in order to avoid any contact between the two layers. Alternatively, it is possible to prepare an internal phase comprising the active ingredient(s) and the fexofenadine and/or at least one pharmaceutically acceptable salt thereof, the grains then being compressed into a single layer in order to obtain a single-layer tablet.

The objective of the invention is in particular to limit the total weight of the galenic form comprising fexofenadine and/or at least one pharmaceutically acceptable salt thereof. The galenic form currently available has a weight of 600 mg. According to the invention, the total weight of the solid unit, excluding any coating or film-coating, is less than 400 mg, preferably less than 300 mg and even more preferentially less than 250 mg, for a fexofenadine content of 180 mg.

This weight limitation of the unit is also possible by virtue of the implementation of the hot-melt process. Unexpectedly, it has been possible to implement this process under conditions which make it possible not to damage the dissolution properties of the solid unit.

In particular, the solid unit exhibits a dissolution of greater than or equal to 80% by weight of fexofenadine and/or of at least one pharmaceutically acceptable salt thereof, preferentially greater than 90% by weight, relative to the total weight of said fexofenadine and/or said at least one pharmaceutically acceptable salt thereof, present in said solid unit, said dissolution percentage being measured at the end of 30 minutes after said solid unit has been placed in a container containing 900 ml of a hydrochloric acid solution at 0.001 N, having a pH equal to 3.0, at a temperature of 37° C. and with stirring at a speed of 50 rpm in a USP Apparatus 2<711>. In particular, the solid unit meets the specification Q=85 after 30 min according to the criteria of the dissolution test described in the US and European pharmacopeias.

Even more particularly, the solid unit exhibits a dissolution of greater than or equal to 60% by weight of fexofenadine and/or of at least one pharmaceutically acceptable salt thereof, preferentially greater than 70% by weight, relative to the total weight of said fexofenadine and/or said at least one pharmaceutically acceptable salt thereof, present in said solid unit, said dissolution percentage being measured at the end of 10 minutes after said solid unit has been placed in a container containing 900 ml of a hydrochloric acid solution at 0.001 N, having a pH equal to 3.0, at a temperature of 37° C. and with stirring at a speed of 50 rpm in a USP Apparatus 2 <711>. In particular, the solid unit meets the specification Q=65 after 10 min according to the criteria of the dissolution test described in the US and European pharmacopeias.

Alternatively, the solid unit exhibits a dissolution of greater than or equal to 70% by weight of fexofenadine and/or of at least one pharmaceutically acceptable salt thereof, preferentially greater than 75% by weight, relative to the total weight of said fexofenadine and/or said at least one pharmaceutically acceptable salt thereof, present in said solid unit, said dissolution percentage being measured at the end of 45 minutes after said solid unit has been placed in a container containing 900 ml of a hydrochloric acid solution at 0.001 N, having a pH equal to 3.0, at a temperature of 37° C. and with stirring at a speed of 50 rpm in an Apparatus 2 in accordance with the European pharmacopeia 2.9.3. In particular, the solid unit meets the European specification Q=80 after 45 min according to the criteria of the dissolution test described in the US and European pharmacopeias.

In the present application, any reference to a country's pharmacopeia is understood to be a reference to the pharmacopeia in force in the country concerned at the date of filing of the present application.

As indicated above, the solid unit may comprise a coating, preferably a film-coating. It has been noted that the film-coating had no impact on the dissolution profile.

The solid unit according to the invention can be used as a medicament, in particular as an antihistamine, a bronchodilator, and/or for the treatment of allergies and/or urticaria. Likewise, the solid unit can be used in the context of a method for treating an allergy or urticaria, said method comprising the administration to a patient of at least one solid unit according to the invention.

A subject of the invention is also a process for manufacturing a solid unit comprising 5 to 500 mg of fexofenadine and/or of at least one pharmaceutically acceptable salt thereof, comprising at least the following steps:

(i) the mixing of:
   45% to 92% by weight of fexofenadine and/or of at least one pharmaceutically acceptable salt thereof, optionally in combination with at least one other active ingredient, with
   4% to 20% by weight of a hot-melt excipient or of a mixture of hot-melt excipients, said hot-melt excipient(s) having a melting point or a glass transition temperature greater than or equal to 35° C. and less than or equal to 115° C., (ii) the granulation of the mixture obtained in step (i) at a temperature which allows the hot-melt excipient(s) to melt or to soften, (iii) the cooling of the grains resulting from step (ii), (iv) the calibration of the grains, (v) the homogenization of the calibrated grains in order to obtain a homogeneous mixture, and (vi) the forming of a solid unit from the homogeneous mixture, the percentages by weight being expressed relative to the total weight of the composition, the sum of the percentages by weight of each ingredient having to reach 100%.

The features of the preferential or advantageous embodiments concerning the doses of fexofenadine and/or of at least one pharmaceutically acceptable salts thereof, the fexofenadine salts, and the active ingredients combined are as indicated above for the solid unit according to the invention.

In particular, in the process according to the invention, the solid unit comprises one or more additional excipient(s), in a content of from 4% to 50% and preferably from 4% to 15% by weight relative to the weight of the composition of the solid unit. According to one alternative preferential embodiment, the percentage by weight of the additional excipient(s) is preferentially included in the range of from 4% to 35% and more preferentially in the range of from 4% to 30% by weight relative to the weight of the composition of the solid unit.

The mixing step (i) can be carried out manually or mechanically in mixers, batchwise or continuously.

According to a first embodiment of the process according to the invention, this process is carried out batchwise, preferably with a granulation step carried out on a fluidized air bed or via co-rotating twin screws.

According to a particularly advantageous second embodiment of the process according to the invention, the process is carried out continuously, preferably with a granulation step carried out via co-rotating twin screws.

More particularly, the granulation step (ii) can be carried out in a continuous granulator with co-rotating screws rotating in a jacketed barrel, for instance in a Consigma 25 Collette® continuous granulator with co-rotating screws, the barrel of which is brought to a temperature of approximately 80 or 110° C., the speed of the screws ranging from 200 to 400 revolutions per minute.

Alternatively, the granulation step (ii) can be carried out in a fluidized air bed by suspending the mixture resulting from step (i) in a stream of hot air.

Of course, other known equipment and other working conditions may be used and are part of the invention (for example, granulation in a mixer at high shear or by compacting).

Step (iii) is a cooling step which can be carried out, for example, by spreading the grains obtained in the granulation step on a plate (or by transfer by extracting) at approximately 20-25° C.

The calibration step (iv) is carried out, for example, on a calibrator equipped, for example, with a screen which has a mesh size of from 0.5 to 2.5 mm. The screen and in particular the mesh size thereof will be chosen according to the desired calibration. Optionally, the additional excipients of the external phase will be added during this step.

The homogenization step (v) can, for example, be carried out using a tumbler mixer.

Finally, the homogenized mixture undergoes a forming step (vi), advantageously forming by compression, using, for example, a Ronchi, Kilian or Korsh rotary press, between 3 and 20 kN, preferably between 3 and 12 kN, with type B or D or alternatively BB punches, the size of which will be determined according to the size and the shape of tablet desired.

The process according to the invention may also comprise, after step (v), a step of coating or film-coating the solid unit, it being possible for this coating or film-coating to be carried out, for example, using various polymers or other appropriate materials, such as those mentioned above for the solid unit.

The process according to the invention can be carried out for preparing a single-layer or multilayer tablet, the multilayer tablet being particularly advantageous when the fexofenadine and/or at least one pharmaceutically acceptable salt thereof is combined with at least one other active ingredient.

In the case of a process for preparing a single-layer tablet, the mixing step (i) comprises the fexofenadine and/or at least one pharmaceutically acceptable salt thereof and the hot-melt excipient and also the optional combined active ingredient(s). Optionally, and as is subsequently indicated, a part of a disintegrant, in particular a part of a superdisintegrant, can be added to the mixture in step (i).

In the case of a process for preparing a multilayer tablet, the fexofenadine and/or at least one pharmaceutically acceptable salt thereof and the hot-melt excipient are mixed, optionally, with a part of a disintegrant. The process according to the invention is then carried out. Given the small size of the resulting tablet, it is possible to carry out one or more additional compression step(s), with the addition of material, enabling the creation of one or more layers around the tablet resulting from the process according to the invention.

Advantageously, in the process according to the invention, the additional excipient(s) is (are) chosen from the group consisting of disintegrants, flow agents, lubricants and/or diluents. This or these additional excipient(s) may be added during the calibration step (iv) and/or during the homogenization step (v).

Advantageously, the disintegrant is chosen from the group consisting of crosslinked polyvinylpyrrolidone, crosslinked carboxymethylcellulose, alginic acid, sodium alginate, sodium carboxymethylcellulose, microcrystalline cellulose, powdered cellulose, sodium croscarmellose, crospovidone, pregelatinized starch, sodium carboxymethyl starch, starch, and mixtures thereof. Preferably, the disintegrants are chosen from the group consisting of pregelatinized starch, microcrystalline cellulose, sodium carboxymethyl starch (preferably of type A or B), and mixtures thereof, more preferentially sodium croscarmellose, crospovidone, and mixtures thereof.

Advantageously, the superdisintegrants are chosen from the group consisting of sodium croscarmellose, crospovidone and sodium carboxymethyl starch (preferably of type A or B).

Likewise, the flow agent is preferentially chosen from the group consisting of silicon dioxide, preferably colloidal silica, magnesium trisilicate, talc, and mixtures thereof.

Preferably, the lubricant is chosen from the group consisting of magnesium stearate, stearic acid, glyceryl tribehenate, sodium stearylfumarate, calcium stearate, glyceryl monostearate, glyceryl palmitostearate, sodium lauryl sulfate, zinc stearate, stearic acid, hydrogenated vegetable oils, polyethylene glycol, sodium benzoate, talc, and mixtures thereof. More preferentially, the lubricant is chosen from the group consisting of sodium stearylfumarate, calcium stearate, magnesium stearate, zinc stearate, sodium benzoate, talc, and mixtures thereof. The lubricant is preferably magnesium stearate.

Advantageously, the diluent is chosen from the group consisting of lactose, celluloses, preferably microcrystalline cellulose, starch, pregelatinized starch, polyols with a melting point greater than 115° C., sucrose, trehalose, calcium phosphate, calcium carbonate, and mixtures thereof.

Since the objective of the invention is to reduce the weight of the solid unit as far as possible, it is understood that the presence of diluent is to be avoided. However, it is possible to introduce diluent to a certain extent, in a content of less than or equal to 40%. The diluent content is preferably equal to 0.

Preferably, the additional excipient or the plurality of additional excipients comprises at least one disintegrant, it being possible for a part of the at least one disintegrant to also be introduced into the mixture during step (i), this making it possible to promote the crumbling of the solid unit after ingestion. Advantageously, the disintegrant is introduced into the composition in a content of between 4% and 15% by weight and preferably 5% to 12% by weight relative to the total weight of the composition.

As indicated above, this disintegrant may be a simple disintegrant or a superdisintegrant.

More preferentially, the composition comprises a second disintegrant, which is a superdisintegrant, introduced into the composition in a content of between 0.5% and 15% by weight and more preferentially between 0.5% and 12% by weight relative to the total weight of the composition.

Advantageously, the total content of disintegrant(s) in the composition is between 4% and 30% by weight relative to the total weight of the composition.

Preferably, the additional excipients are:
- at least one disintegrant chosen from crospovidone, sodium croscarmellose and/or sodium carboxymethyl starch, microcrystalline cellulose,
- a lubricant: magnesium stearate,
- a flow agent: colloidal silica, and/or
- a diluent chosen from lactose and/or microcrystalline cellulose.

Preferably, the additional excipients are therefore:
- at least one disintegrant chosen from crospovidone, sodium croscarmellose and/or microcrystalline cellulose,
- a lubricant: magnesium stearate,
- a flow agent: colloidal silica, and/or
- a diluent chosen from lactose and/or microcrystalline cellulose.

More preferentially, the additional excipients are:
- at least one disintegrant chosen from crospovidone, sodium croscarmellose and/or microcrystalline cellulose,
- a lubricant: magnesium stearate, and/or
- a flow agent: colloidal silica.

As hot-melt excipient, mention may be made of citric acid monohydrate, stearic acid, palmitic acid, lauric acid, myristic acid, hydrogenated castor oil, hydrogenated vegetable oil, stearyl alcohol, cetostearyl alcohol, cetyl alcohol, vanillin, amorphous chlorocresol, cetyl pyridinium hydrochloride, sorbitan monostearate, sorbitan monopalmitate, xylitol, dextrose, ethylmaltol, butylated hydroxyanisole, benzalkonium hydrochloride, ascorbyl palmitate, sorbitol, anhydrous raffinose, phenylmercuric borate, polyethylene glycols (abbreviated as PEG), such as PEG 3000, PEG 4000, PEG 6000, PEG 8000 and PEG 20 000, polyethylene oxides, polyethylene/propylene glycol copolymers, such as poloxamer 188, poloxamer 237, poloxamer 338, or poloxamer 407, glyceryl monostearate, glyceryl palmitostearate, glyceryl behenate, for instance Compritol®888 ATO, waxes, for instance carnauba wax, microcrystalline wax, white wax or yellow wax, beeswax, sodium acetate trihydrate, polymethacrylates, in particular Eudragit® E, polyvinyl acetate phthalate, carbomers, polycarbophils, hypromellose acetate succinate, copovidone, and mixtures thereof.

Advantageously, the hot-melt excipient(s) is (are) chosen from stearic acid, palmitic acid, hydrogenated castor oil, hydrogenated vegetable oil, stearyl alcohol, vanillin, amorphous chlorocresol, cetyl pyridinium hydrochloride, sorbitan monopalmitate, xylitol, dextrose, ethylmaltol, ascorbyl palmitate, sorbitol, anhydrous raffinose, phenylmercuric borate, polyethylene glycols (abbreviated as PEG), polyethylene oxides, polyethylene/propylene glycol copolymers, such as poloxamer 188, poloxamer 237, poloxamer 338, or poloxamer 407, glyceryl monostearate, glyceryl palmitostearate, glyceryl behenate, waxes, for instance carnauba wax, microcrystalline wax, white wax or yellow wax, beeswax, sodium acetate trihydrate, polymethacrylates, in particular Eudragit® E, carbomers, polycarbophils, hypromellose acetate succinate, and mixtures thereof.

Preferably, the hot-melt excipient(s) is (are) chosen from stearic acid, palmitic acid, hydrogenated castor oil, xylitol, polyethylene glycols (abbreviated as PEG, such as PEG 4000, PEG 6000 and PEG 8000), polyethylene oxides, polyethylene/propylene glycol copolymers, such as poloxamer 188, poloxamer 237, poloxamer 338 or poloxamer 407, glyceryl monostearate, glyceryl palmitostearate, glyceryl behenate, carnauba wax, microcrystalline wax, white wax or yellow wax, beeswax, polymethacrylates, in particular Eudragit® E, and mixtures thereof.

Even more preferentially, the hot-melt excipient(s) is (are) chosen from polyethylene/propylene glycol copolymers, polyethylene glycols, stearic acid, polyethylene oxides, glyceryl palmitostearate, and mixtures thereof.

It will be noted that, in the context of the process, certain additional excipients, such as lubricants, can also be used as hot-melt excipients. However, these two categories of excipients are perfectly identifiable in the context of a process, since an excipient used as a hot-melt excipient will, during the process, be in a softened or molten form, whereas the same excipient used as an additional excipient, for instance as a lubricant, will be in the form of a powder.

Advantageously, the hot-melt excipient(s) has (have) a viscosity at 100° C. with a shear of $0.1\ s^{-1}$ of less than 3000 mPa·s, preferably less than 2000 mPa·s or more preferentially than 1000 mPa·s.

The measurement of the viscosity is a measurement well known to those skilled in the art. In the present case, it is carried out using a rheometer (of Anton Paar type). The hot-melt excipient is brought to the desired working temperature, namely 100° C. for the present measurement, prior to the measurement. It is subsequently introduced into a cylindrical container thermostatted at the desired working temperature, so as to be subjected to, therein, a shear ramp (from $0.1\ s^{-1}$ to $100\ s^{-1}$) applied by means of a coaxial module.

Preferably, the hot-melt excipient(s) is (are) water soluble.

According to one advantageous embodiment, the ratio of the fexofenadine and/or of at least one pharmaceutically acceptable salt thereof, such as fexofenadine hydrochloride, to the hot-melt excipient(s) is between 3.5 and 15, preferably between 5 and 12, more preferentially between 8 and 10 or, according to one alternative preferential embodiment, between 7 and 10.

Preferably, the percentage by weight of the hot-melt excipient(s) having a melting point or a glass transition temperature greater than or equal to 35° C. and less than or equal to 115° C. is included in the range of from 4% to 17% by weight and more preferentially from 4% to 15% by weight. It is therefore important for the total content of the excipient(s) used as hot-melt excipient to be no greater than 20%, preferably no greater than 17% and more preferentially no greater than 15%.

According to preferential embodiments, the solid unit prepared by means of the process according to the invention has the specific compositions mentioned above for the solid unit.

The objective of the process according to the invention is in particular to manufacture a solid unit which has a weight less than that of the galenic form currently available. The weight and dissolution characteristics of the solid unit directly obtained by means of the process according to the invention are as stated above for the solid unit according to the invention.

EXAMPLES

The following example describes the preparation of solid units in accordance with the invention. This example is not limiting and merely illustrates the present invention.

The percentages of the compounds below are expressed, unless otherwise indicated, by weight relative to the total weight of the composition or of the solid unit which contains them, as appropriate.

1. Compositions of Tablets According to the Invention

By way of example, four pharmaceutical compositions 1A to 1D according to the invention, using PEG 6000 as hot-melt excipient and comprising only fexofenadine hydrochloride as active ingredient, are indicated by way of illustration in table 1 below.

The nature of the ingredients of these compositions is indicated in said table, as is the content of said ingredients, expressed as % by weight of ingredient relative to the total weight of the composition/of the solid unit.

TABLE 1

| | | Composition | | | |
|---|---|---|---|---|---|
| | | 1A | 1B | 1C | 1D |
| Internal phase | Fexofenadine hydrochloride | 83.79% | 45.31% | 78.88% | 79.38% |
| | PEG 6000 | 9.31% | 5.03 | 9.32% | 8.82% |
| | Sodium croscarmellose | / | / | 5.00% | / |
| External phase | Crospovidone | 5.00% | 10.00% | / | / |
| | Sodium croscarmellose | / | / | 5.00% | 10.00% |
| | Magnesium stearate | 0.95% | 0.95% | 0.90% | 0.90% |
| | Colloidal silica | 0.95% | 0.95% | 0.90% | 0.90% |
| | Microcrystalline cellulose | / | 11.33% | / | / |
| | Lactose | / | 26.43% | / | / |

The composition comprises an "external" phase and an "internal" phase. The ingredients of the internal phase are used to manufacture the grain comprising the fexofenadine hydrochloride. The ingredients of the external phase are additional excipients, which make it possible, for example, to improve the processability of the formulation.

The ratio of fexofenadine hydrochloride to hot-melt excipient in compositions 1A to 1D is respectively equal to 9, 9, 8.5 and 9.

2. Compositions of Internal Phase According to the Invention Comprising Various Hot-Melt Excipients Other grains (internal phase) were obtained using fexofenadine hydrochloride as active ingredient and hot-melt excipients other than PEG 6000. These examples of grain formulations 1E to 1H are given in table 2 below:

TABLE 2

| | Composition | | | |
|---|---|---|---|---|
| | 1E | 1F | 1G | 1H |
| Fexofenadine hydrochloride | 90.00 | 90.00 | 90.00 | 90.00 |
| Stearic acid | 10.00 | / | / | / |
| Precirol ® (glyceryl palmitostearate) | / | 10.00 | / | / |
| Poloxamer 407 | / | / | 10.00 | / |
| Polyox ® (polyethylene oxide) | / | / | / | 10.00 |

The weight ratio of fexofenadine hydrochloride to hot-melt excipients in compositions 1E to 1H is 9.

3. Alternative Compositions According to the Invention

In a manner similar to example 1, two other pharmaceutical compositions 2A and 2B were prepared according to the invention and are indicated by way of illustration in table 3 below.

The nature of the ingredients of these compositions is indicated in said table, as is the content of said ingredients, expressed as % by weight of ingredient relative to the total weight of the composition/of the solid unit.

TABLE 3

| | | Composition | |
|---|---|---|---|
| | | 2A | 2B |
| Internal phase | Fexofenadine hydrochloride | 63.50% | 70.63% |
| | PEG 6000 | 8.82% | 8.72% |
| | Pregelatinized starch | 10.58% | 7.85% |
| | Microcrystalline cellulose | 5.29% | / |
| External phase | Sodium carboxymethyl starch (type A) | 10.00% | / |
| | Sodium croscarmellose | / | 1.00% |
| | Magnesium stearate | 0.90% | 0.90% |
| | Colloidal silica | 0.90% | 0.90% |
| | Microcrystalline cellulose | / | 10.00% |

The ratio of fexofenadine hydrochloride to hot-melt excipient in compositions 2A and 2B is respectively equal to 7.2 and 8.1.

4. Manufacturing Process

Tablets were manufactured using compositions 1A to 1H, 2A and 2B mentioned above and according to the process described below.

The composition of the tablets 1E to 1H is indicated in table 4 below:

TABLE 4

| | | Composition 1E-1H |
|---|---|---|
| Internal phase | Fexofenadine hydrochloride | 79.38% |
| | Hot-melt excipient | 8.82% |
| External phase | Crospovidone | 10.00% |
| | Magnesium stearate | 0.90% |
| | Colloidal silica | 0.90% |

A mixing step (i) of said process consists in mixing the ingredients of the internal phase of one of compositions 1A to 1H, 2A and 2B mentioned above, using a Turbula® or Servolift® tumbler mixer for approximately 210 revolutions.

A granulation step (ii), which may be in continuous or batchwise mode, is then carried out. The continuous mode is carried out, for example, using a Consigma® 25 granulator with co-rotating screws rotating in a jacketed barrel. The batchwise mode is carried out, for example, using a fluidized air bed.

For the granulator of Consigma® type, the parameters are:
- a powder mixture flow rate of 5 to 6 kg/h,
- a screw speed of 200 to 400 revolutions per minute, and
- a jacket temperature of 80 to 120° C.

For the fluidized air bed, the parameters are:
- an air flow rate of 20 to 400 m³/hour depending on the type of fluidized air bed used, and
- a set heating temperature between 35° C. and 130° C. depending on the hot-melt excipient used.

A cooling step (iii) then consists in cooling to approximately 20-25° C. by spreading on a plate or by pneumatic transport of said grains.

Then, a calibration step (iv) is carried out on a Frewitt® TC-150 calibrator using a screen with a 1.5 mm mesh size.

Magnesium stearate, colloidal silica, crospovidone and/or any other additional excipient are optionally added to the grains during step (iv). As appropriate, the mixing of the grains and the additional excipients is carried out for approximately 210 revolutions in a Turbula® ou Servolift® tumbler mixer for homogenization (v).

Finally, the homogenized mixture undergoes a forming step (vi) by compression using a Korsh® XL 100 rotary press, a Kilian S100 rotary press or a Ronchi rotary press, with a compressive force of between 3 and 20 kN.

Table 5 below groups together the characteristics of the tablets obtained at the end of a continuous or batchwise process, using the compositions respectively described above, and also the characteristics of the reference tablet obtained by wet granulation. More particularly, table 5 indicates, for each tablet, its total weight, its weight of fexofenadine hydrochloride and the percentage reduction in weight of the tablet relative to the reference tablet.

TABLE 5

| Tablet | 1A | 1B | 1C | 1D to 1H | 2A | 2B | Reference |
|---|---|---|---|---|---|---|---|
| Weight of the tablet (mg) | 214.82 | 397.24 | 228.19 | 226.76 | 283.45 | 254.84 | 600.00 |
| Weight of fexofenadine hydrochloride (mg) | 180.00 | 180.00 | 180.00 | 180.00 | 180.00 | 180.00 | 180.00 |
| % reduction in weight | 64.2 | 33.8 | 62.0 | 62.2 | 52.8 | 57.5 | / |

Reference: Allegra ®

Thus, for the same amount of active ingredient, the compositions according to the invention have a reduced weight and a reduced size compared with the reference tablet.

5. Hardness of the Tablets Obtained According to the Invention

The hardness of the tablets is measured using a durometer. Each tablet is positioned between the two jaws of the durometer. The value of the force in Newtons, exerted on the tablet, obtained during the crushing of the tablet is noted. The average value of the hardnesses recorded on the durometer is indicated in table 6 below.

TABLE 6

| Tablet | 1A to 1D | 1E | 1F | 1G | 1H | 2A and 2B |
|---|---|---|---|---|---|---|
| Hardness (N) | ≈100 | ≈100 | ≈65 | ≈80 | ≈50 | ≈100 |

6. Dissolution of the Active Ingredient Contained in the Tablets According to the Invention

6.1. Procedure for Measuring the Dissolution of the Active Ingredient:

A tablet is placed in a container containing 900 ml of non-degassed solution at pH 3.0 (0.001 N HCl) and at a temperature of 37° C. The stirring speed in the container is fixed at 50 rpm by means of a paddle. More particularly, the dissolution test is carried out using an Apparatus 2 in accordance with the European pharmacopeia 2.9.3 and with the United States pharmacopeia (USP)<711>.

The amount of active ingredient dissolved as a function of time is measured by HPLC (high-performance liquid chromatography) assay, for example according to a methodology in accordance with the European pharmacopeia 2.2.29, "Liquid chromatogrphy" or in accordance with the United States pharmacopeia (USP) 621 "Chromatography". Such a measurement is well known to those skilled in the art.

6.2. Results

The weight percentage of fexofenadine hydrochloride dissolved for examples 1A, 1B and 1D and the reference are given in table 7 below.

TABLE 7

| Tablet | 1A | 1B | 1D | 1E | 1F | 1H | 2A | 2B | Reference |
|---|---|---|---|---|---|---|---|---|---|
| % dissolved at t = 10 min | 92.8 | 92.9 | 98.6 | 85.3 | 69.3 | 63.1 | 90.8 | 66.5 | 82.6 |
| % dissolved at t = 30 min | 96.0 | 95.5 | 101.8 | 92.3 | 80.0 | 80.0 | 96.5 | 85.0 | 93.1 |
| % dissolved at t = 45 min | 97.1 | 96.2 | 102.1 | 93.8 | 82.0 | 85.2 | 97.8 | 88.3 | 94.7 |

Reference: Allegra® 180 mg.

The dissolution profiles between the various examples and the reference are comparable and all the examples are in accordance with the European specification of the product.

The invention claimed is:

1. A solid unfractionated unit comprising a dose of 5 to 500 mg of fexofenadine, or a pharmaceutically acceptable salt thereof, the composition of which is the following:
   - 45% to 92% by weight of fexofenadine, or a pharmaceutically acceptable salt thereof, optionally in combination with at least one other active ingredient;
   - 4% to 20% by weight of a hot-melt excipient or mixture of hot-melt excipients, said hot-melt excipient(s) selected from the group consisting of polyethylene glycol and stearic acid; and
   - 4% to 50% by weight of an additional excipient or of a plurality of additional excipients, the percentages by weight being expressed relative to the total weight of the composition.

2. The solid unfractionated unit according to claim 1, wherein the weight ratio of fexofenadine, or a pharmaceutically acceptable salt thereof, to the hot-melt excipient(s) is between 3.5 and 15.

3. The solid unfractionated unit according to claim 1, wherein the percentage by weight of fexofenadine, or a pharmaceutically acceptable salt thereof, is between 55% and 92%.

4. The solid unfractionated unit according to claim 1, wherein the percentage by weight of the hot-melt excipient(s) is in the range of from 4% to 17%.

5. The solid unfractionated unit according to claim 1, wherein the percentage by weight of the additional excipient(s) is in the range of from 4% to 35%.

6. The solid unfractionated unit according to claim 1, wherein the additional excipient(s) is (are) chosen from the group consisting of disintegrants, flow agents, lubricants and diluents.

7. The solid unfractionated unit according to claim 1, wherein the total weight of the solid unfractionated unit, excluding any coating or film-coating, is less than 400 mg, for a fexofenadine content of 180 mg.

8. A pharmaceutical composition comprising the solid unfractionated unit of claim 1.

9. A process for manufacturing a solid unfractionated unit comprising 5 to 500 mg of fexofenadine, or a pharmaceutically acceptable salt thereof, the process comprising at least the following steps:
   (i) the mixing of:
   - 45% to 92% by weight of fexofenadine, or a pharmaceutically acceptable salt thereof, optionally in combination with at least one other active ingredient, with
   - 4% to 20% by weight of a hot-melt excipient or of a mixture of hot-melt excipients, said hot-melt excipient(s) selected from the group consisting of polyethylene glycol and stearic acid;
   (ii) the granulation of the mixture obtained in step (i) at a temperature which allows the hot-melt excipient(s) to melt or to soften;
   (iii) the cooling of the grains resulting from step (ii);
   (iv) the calibration of the grains;
   (v) the homogenization of the calibrated grains in order to obtain a homogeneous mixture; and
   (vi) the forming of a solid unit from the homogeneous mixture, the percentages by weight being expressed relative to the total weight of the composition.

10. The process as claimed in claim 9, wherein the solid unfractionated unit further comprises an additional excipient or a plurality of additional excipients, in a content of from 4% to 50% by weight relative to the total weight of the solid unfractionated unit.

11. The process as claimed in claim 10, wherein the additional excipient(s) is (are) chosen from the group consisting of disintegrants, flow agents, lubricants and diluents, and which can be added during the calibration step (iv) and/or during the homogenization step (v).

12. The process according to claim 10, wherein the additional excipient(s) comprise(s) at least one disintegrant, wherein at least a part of the at least one disintegrant is introduced into the mixture during step (i).

13. The process according to claim 9, further comprising, after step (v), a step of coating or film-coating the solid unfractionated unit.

14. A method of treating allergies and/or urticaria in a patient in need thereof comprising administering the solid unfractionated unit of claim 1 to the patient in need thereof.

15. The solid unfractionated unit according to claim 1, comprising 78.88% fexofenadine hydrochloride, 9.32% PEG 6000, 10.00% sodium croscarmellose, 0.90% magnesium stearate, and 0.90% colloidal silica.

16. The solid unfractionated unit according to claim 1, comprising 63.50% fexofenadine hydrochloride, 8.82% PEG 6000, 10.58% pregelatinized starch, 5.29% microcrystalline cellulose, 10.00% sodium carboxymethyl starch, 0.90% magnesium stearate, and 0.90% colloidal silica.

17. The solid unfractionated unit according to claim 1, comprising 70.63% fexofenadine hydrochloride, 8.72% PEG 6000, 7.85% pregelatinized starch, 1.00% sodium croscarmellose, 0.90% magnesium stearate, 0.90% colloidal silica, and 10.00% microcrystalline cellulose.

18. The solid unfractionated unit according to claim 1, the composition of which is the following:
   - 70% to 92% by weight of fexofenadine, or a pharmaceutically acceptable salt thereof, optionally in combination with at least one other active ingredient;

4% to 15% by weight of a hot-melt excipient or mixture of hot-melt excipients, said hot-melt excipient(s) selected from the group consisting of polyethylene glycol and stearic acid; and 4% to 15% by weight of an additional excipient or of a plurality of additional excipients, the percentages by weight being expressed relative to the total weight of the composition.

19. The solid unfractionated unit according to claim 1, the composition of which is the following:

60% to 92% by weight of fexofenadine, or a pharmaceutically acceptable salt thereof, optionally in combination with at least one other active ingredient;

4% to 10% by weight of a hot-melt excipient or mixture of hot-melt excipients, said hot-melt excipient(s) selected from the group consisting of polyethylene glycol and stearic acid; and 4% to 30% by weight of an additional excipient or of a plurality of additional excipients, the percentages by weight being expressed relative to the total weight of the composition.

* * * * *